(12) United States Patent
Power

(10) Patent No.: US 12,144,923 B2
(45) Date of Patent: *Nov. 19, 2024

(54) AEROSOL DELIVERY SYSTEM WITH HUMIDIFICATION

(71) Applicant: Stamford Devices Limited, Dangan (IE)

(72) Inventor: Patrick Power, Galway (IE)

(73) Assignee: Stamford Devices Limited, Galway (IE)

( * ) Notice: Subject to any disclaimer, the term of this patent is extended or adjusted under 35 U.S.C. 154(b) by 69 days.

This patent is subject to a terminal disclaimer.

(21) Appl. No.: 17/818,549

(22) Filed: Aug. 9, 2022

(65) Prior Publication Data

US 2023/0321368 A1  Oct. 12, 2023

Related U.S. Application Data

(63) Continuation of application No. 16/853,039, filed on Apr. 20, 2020, now Pat. No. 11,433,189, which is a (Continued)

(30) Foreign Application Priority Data

Jun. 10, 2014 (EP) .................................... 14171765

(51) Int. Cl.
*A61M 11/02* (2006.01)
*A61M 11/00* (2006.01)
(Continued)

(52) U.S. Cl.
CPC ............. *A61M 11/02* (2013.01); *A61M 11/00* (2013.01); *A61M 11/06* (2013.01);
(Continued)

(58) Field of Classification Search
CPC .... A61M 16/00; A61M 16/16; A61M 16/161; A61M 16/024; A61M 16/1075–1095;
(Continued)

(56) References Cited

U.S. PATENT DOCUMENTS 4,805,609 A  2/1989 Roberts et al.
5,237,987 A  8/1993 Anderson et al.
(Continued)

FOREIGN PATENT DOCUMENTS

WO  WO 2009/042187 A1  4/2009
WO  WO 2013/165263 A1  11/2013

OTHER PUBLICATIONS

International Search Report and Written Opinion in corresponding International Application No. PCT/EP2015/062972 mailed Aug. 7, 2015 (10 pages).

*Primary Examiner* — Cody J Lieuwen
(74) *Attorney, Agent, or Firm* — Bookoff McAndrews, PLLC

(57) ABSTRACT

An aerosol delivery system has a nebulizer and a humidifier providing a gas flow to the nebulizer. A controller varies humidity level of the gas flow to the nebulizer so that if the nebulizer is not operating it has about 100% humidity and it is operating the value is less to allow for the humidification effect of the nebulizer. The control may be achieved by dynamically varying proportions of flow through a dry branch and a humidification branch.

20 Claims, 2 Drawing Sheets

Figure 1:
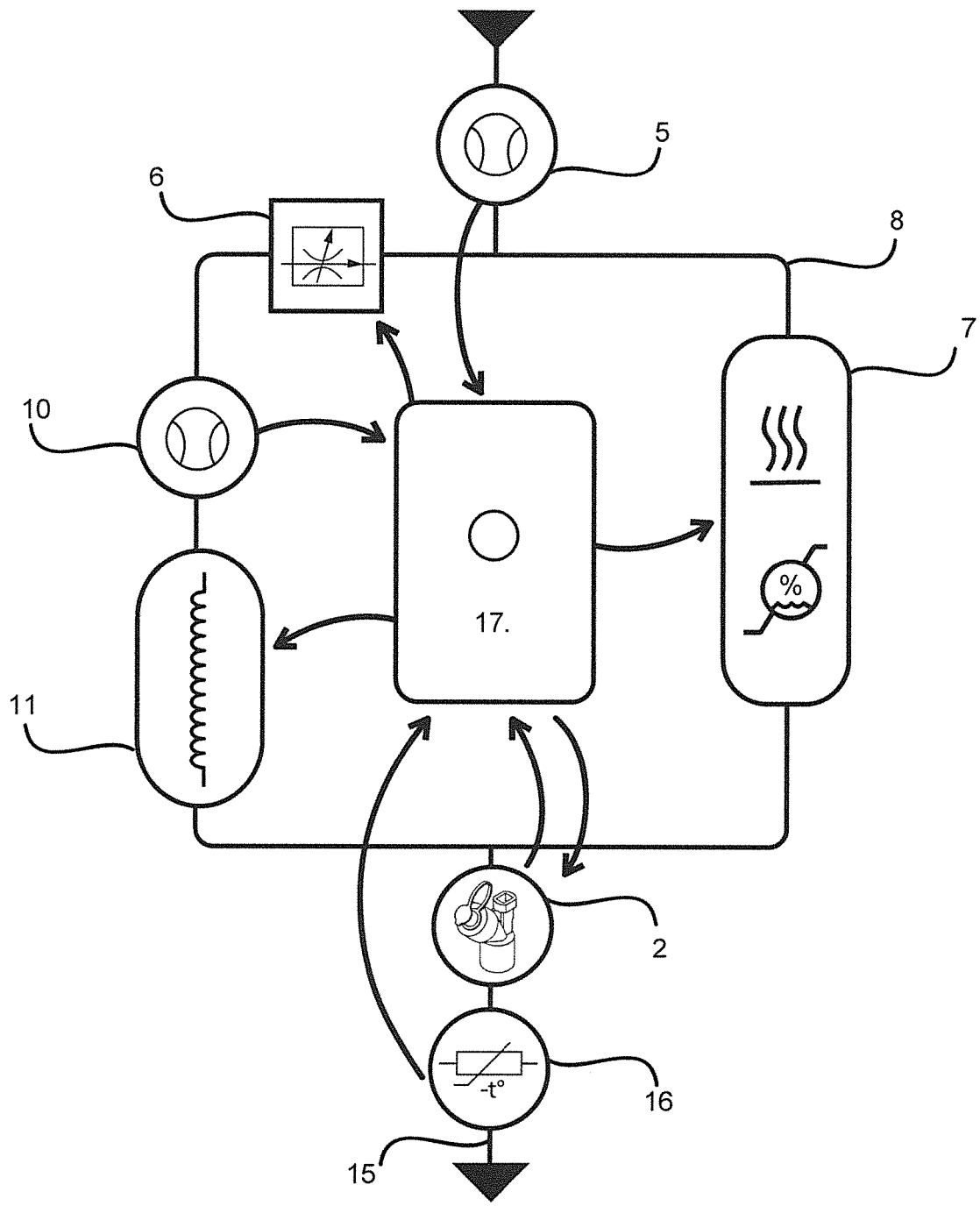

Related U.S. Application Data continuation of application No. 15/300,513, filed as application No. PCT/EP2015/062972 on Jun. 10, 2015, now Pat. No. 10,661,031.

(51) Int. Cl.
*A61M 11/06* (2006.01)
*A61M 16/00* (2006.01)
*A61M 16/16* (2006.01)

(52) U.S. Cl.
CPC .......... *A61M 16/024* (2017.08); *A61M 16/16* (2013.01); *A61M 16/161* (2014.02)

(58) Field of Classification Search
CPC .. A61M 16/1045; A61M 11/00; A61M 11/02; A61M 11/06; A61M 11/04–042; A61M 11/005
See application file for complete search history.

(56) References Cited

U.S. PATENT DOCUMENTS

| | | | |
|---|---|---|---|
| 5,388,571 A | 2/1995 | Roberts et al. | |
| 7,146,979 B2* | 12/2006 | Seakins | A61M 16/1075 128/204.17 |
| 7,934,498 B1 | 5/2011 | Heidelberger | |
| 2005/0229928 A1 | 10/2005 | Ivri et al. | |
| 2005/0247305 A1 | 11/2005 | Zierenberg et al. | |
| 2007/0137646 A1* | 6/2007 | Weinstein | A62B 9/003 128/204.17 |
| 2008/0000470 A1* | 1/2008 | Minocchieri | A61M 16/0003 128/200.21 |
| 2012/0125334 A1* | 5/2012 | Korneff | A61M 16/109 128/203.26 |
| 2013/0263852 A1 | 10/2013 | Montgomery | |
| 2015/0107588 A1* | 4/2015 | Cheung | A61M 16/0066 128/203.14 |

* cited by examiner

AEROSOL DELIVERY SYSTEM WITH HUMIDIFICATION

CROSS-REFERENCE TO RELATED APPLICATIONS

This application is a continuation of U.S. application Ser. No. 16/853,039, filed on Apr. 20, 2020, which is a continuation of U.S. application Ser. No. 15/300,513, filed on Sep. 29, 2016, which is a U.S. national phase entry under 35 U.S.C. § 371 of International Application No. PCT/EP2015/062972, filed on Jun. 10, 2015, which claims priority to European Patent Application No. 14171765.2, filed on Jun. 10, 2014. The contents of all of the above patent applications are incorporated herein by reference in their entirety.

INTRODUCTION

The invention relates to aerosol delivery systems (or "nebulizers") with humidification.

WO2013/165263 describes a respiratory humidifier in which a flow generator communicates with a humidifier, and a user interface on the humidifier displays data from a nebulizer of a pulse oximeter.

WO2009/042187 (Nektar Therapeutics) describes a system to introduce aerosolized medicament to a patient which includes a dehumidifier coupled to an inspiratory limb of a ventilator circuit.

An object of the invention is to achieve improved efficiency and reliability in drug delivery.

SUMMARY OF THE INVENTION

According to the invention, there is provided an aerosol delivery system comprising a nebulizer and a humidifier for a nebulizer gas flow, wherein the system comprises a controller configured to vary humidity level of the nebulizer gas flow.

In one embodiment, the controller is configured to reduce the humidity level of gas fed to the nebulizer during nebulizer active time. In one embodiment, the system comprises a sensor for detecting when the nebulizer is active applying medication to the gas flow, and the controller is configured to reduce humidity level of the gas flow to the nebulizer during said active time. In one embodiment the sensor comprises a vision system monitoring plume at the nebulizer.

In one embodiment, the controller is configured to assess the rate at which a nebulizer reservoir liquid volume decreases to calculate the nebulizer output rate.

In one embodiment, the controller is configured to control humidity of the nebulizer gas flow so that the nebulizer brings the relative humidity up to a target level such as about 100% provided to a patient. In one embodiment, the controller is configured to vary humidification according to nebulization rate. In one embodiment, the controller is configured to vary humidification according to gas flow rate.

In one embodiment, the humidifier has a variable output. In one embodiment, the humidifier has a water conduit and a controller for varying water flow rate.

In one embodiment, the system comprises a humidification branch and a dry supply branch linked to the nebulizer, and a flow controller for varying proportions in the branches. In one embodiment, the controller is configured to determine when the nebulizer is active applying medication to the gas flow, and to reduce humidity level during said active time by varying proportions in the branches.

In one embodiment, the system further comprises a temperature sensor to sense temperature of gas flow downstream of the nebulizer, and the controller is configured to use said sensed temperature as an input to vary said humidity level.

In one embodiment, the controller is configured to adjust temperature of gas reaching the nebulizer such that nebulizer output flow has a target temperature.

In one embodiment, the system further comprises a humidity sensor to sense humidity of gas flow downstream of the nebulizer, and the controller is configured to use said sensed humidity as an input to vary said gas flow humidity level.

In one embodiment, the controller is configured to vary nebulizer output rate to vary humidity of nebulizer output flow.

In another aspect, the invention provides a method of controlling an aerosol delivery system having a nebulizer and a humidifier for a nebulizer gas flow, the method comprising varying humidity level of the nebulizer gas flow.

In one embodiment, the method comprises the steps of determining when the nebulizer is active applying medication to the gas flow, and reducing humidity level of the gas flow to the nebulizer during said active time. In one embodiment, the humidity is controlled so that the nebulizer brings the humidity up to a target level provided to a patient. In one embodiment, said target level is about 100%

In one embodiment, the method comprises varying humidification according to nebulization rate.

In one embodiment, the method comprises varying humidification according to gas flow rate.

In one embodiment, a humidifier with a variable output is controlled.

In one embodiment, the system comprises a humidification branch and a dry supply branch, both of said branches linked to the nebulizer, and the controller varies proportions of flow in the branches.

In one embodiment, the controller determines when the nebulizer is active applying medication to the gas flow, and reduces humidity level during said active time, by varying proportions in the branches.

In one embodiment, the system further comprises a temperature sensor to sense temperature of flow downstream of the nebulizer, and the controller uses said sensed temperature as an input to vary said humidity level.

In one embodiment, the controller adjusts temperature of gas reaching the nebulizer such that nebulizer output gas has a target temperature.

In one embodiment, the system further comprises a humidity sensor to sense temperature of flow downstream of the nebulizer, and the controller uses said sensed humidity as an input to vary said gas flow humidity level.

According to the invention there is provided an aerosol delivery system comprising a nebulizer and a humidifier feeding the nebulizer, wherein the system comprises a controller for varying humidity level of gas fed to the nebulizer.

In one embodiment, the system comprises a sensor for detecting when the nebulizer is active applying medication to the gas flow, and the controller is configured to reduce humidity level during said active time.

In one embodiment, the humidity is controlled so that the nebulizer brings the relative humidity up to a target level such as about 100% provided to a patient.

In one embodiment, the controller is configured to vary humidification according to nebulization rate. In one embodiment, the controller is configured to vary humidification according to gas flow rate.

In one embodiment, the humidifier has a variable output. Preferably, the humidifier has a water conduit and a controller for varying water flow rate.

In one embodiment, the system comprises a humidification branch and a dry supply branch feeding the nebulizer, and a flow controller for varying proportions in the branches.

In another aspect, the invention provides a method of controlling an aerosol delivery system having a nebulizer, the method comprising varying humidity level of gas fed to the nebulizer.

In one embodiment, the method comprises detecting when the nebulizer is active applying medication to the gas flow, and reducing humidity level during said active time.

In one embodiment, the humidity is controlled so that the nebulizer brings the relative humidity up to a target level such as about 100% provided to a patient.

In one embodiment, the method comprises varying humidification according to nebulization rate.

In one embodiment, the method comprises varying humidification according to gas flow rate.

In one embodiment, a humidifier with a variable output is controlled.

In one embodiment, the system comprises a humidification branch and a dry supply branch feeding the nebulizer, and the method varies proportions of flow in the branches.

DETAILED DESCRIPTION OF THE INVENTION

The invention will be more clearly understood from the following description of some embodiments thereof, given by way of example only with reference to the accompanying drawings in which—

Figure 2:
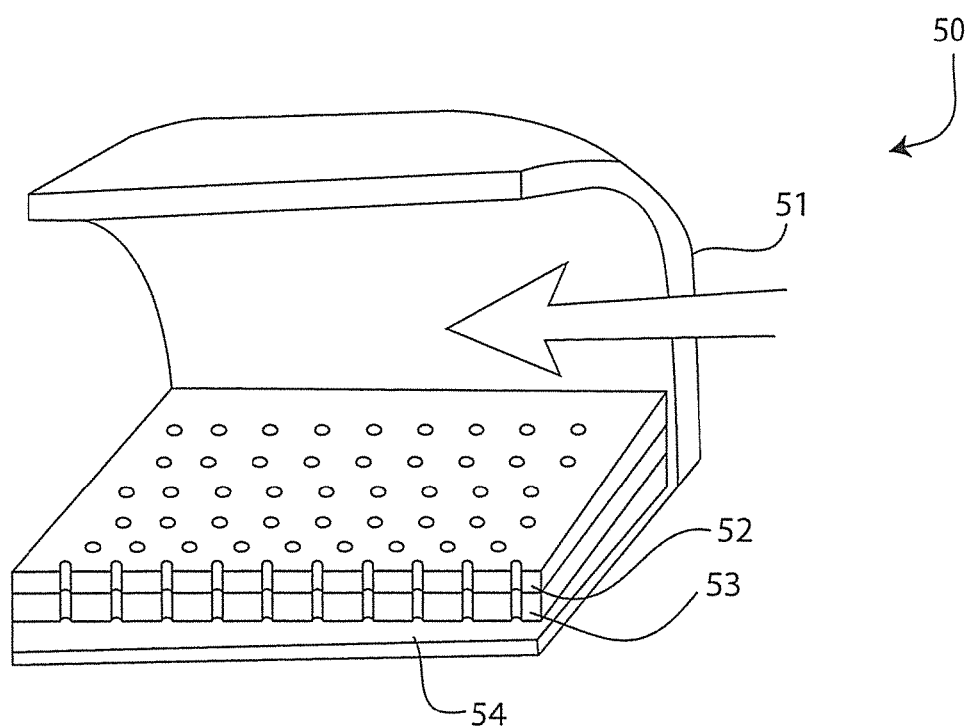

FIG. 1 is a block diagram illustrating an aerosol delivery system of the invention, in which two branches feed a nebulizer; and FIG. 2 is a partly cut-away perspective view showing a humidifier of an alternative system, the humidifier having a variable humidity output.

Referring to FIG. 1 an aerosol delivery system 1 comprises a nebulizer 2. Gas is supplied to the nebulizer 2 via an inlet 5 incorporating a gas pressure sensor operating up to about 80cmH$_2$O. An alternative to this component is a flow sensor, which would operate up to about 150l/min.

The flow from the inlet 5 is divided into two branches as follows:

(a) A valve/flow restrictor 6 to govern flow towards a pressure sensor 10 feeding a heater 11. The valve 6 restricts flow so that it dictates what percentage of flow entering the system via the inlet 5 is directed down each limb. The sensor 10 is optional, in this embodiment, serving as a check that the valve is allowing the right amount of gas to flow through. The valve 6 component may in other embodiments be a variable flow restrictor. The components 6 and 10 could be on either limb. They are included to ensure that the correct ratio of the incoming gas flow goes down each limb, and as such could work as well on either or both limbs.

It may also be beneficial to have a valve/flow restrictor immediately after the valve 5 to remove the need for the user (e.g. clinician) to use an external gas flow regulator.

(b) A humidifier 7 incorporating a heater linked to the inlet 5 by a biocompatible tube 8. The components may or may not be connected by tubing, for example they may be connected directly to each other, and where there is a tube it may not be biocompatible.

The branches, namely the outlets of the heater 11 and of the humidifier 7, are joined at the nebulizer 2 inlet.

The nebulizer 2 aerosolizes a liquid (water, saline, therapeutics, etc.) into the gas flow and via a temperature and/or humidity sensor 16 through an outlet line 15 to a patient interface.

The inlet 5 is in one embodiment a digital, in-line, fast update, self-calibrating sensor such as the Sensirion SFM3000™ (http://www.sensirion.com/en/products/mass-flow-meters-for-gases/mass-flow-meter-sfm3000/) or similar. However, any flow sensor capable of detecting flows of 0-150 lpm+/−10% or pressure sensor capable of detecting accurately 80cmH$_2$O would suffice. These sensors will establish flow through either infrared, thermal senor, chemical, mechanical or pressure means.

The valve/flow restrictor 6 is in one embodiment an electronically modulating flow control gas valve, to provide the required accuracy required for this system. A single valve may not be optimum to cover the entire range of flows required for this application, and so it may require two. For example a Proportionair FQB3™ control valve would cover flows greater than 28 lpm and the FQPV™ control valve for lower flow rates. Both these valves can be provided with a Proportionair F-Series™ flow sensor so that component would provide the functionality of the component 10.

The inlet 5 could also comprise such a valve/sensor pair.

The humidifier 7 comprises a water reservoir and a means of heating. This can be as simple as a liquid feed onto a hotplate, or a more complex arrangement such as the humidifier 50 described below.

The heater 11 is of the known type having a helical coil heating element to maximise surface area exposed to the gas flow. Alternatively, the heater could be of the type having a heated metallic or ceramic cylinder through which the gas flows.

There is a controller, 17, linked to the illustrated system components. This dynamically controls the valve 6 to govern the proportions of gas flow in the two branches. The inlet 5 measures the gas flow into the system.

It is known that adequate humidification of ventilator patient circuits is essential to maintaining mucociliary clearance levels within the patient airways. As humidity levels decrease below optimal (44 mg/l) cilia activity reduces causing slower mucociliary clearance leading to secretion drying and accumulation. This manifests as patient discomfort, coughing, reduced lung function and potentially airway occlusion. High relative humidity levels reduce the carrying capacity of the gas resulting in less bacteria and viruses being transported into the airways.

As air passes through a standard humidified circuit temperature fluctuations and/or aerosol is added and this results in a humidity drop (absolute and/or relative) and/or precipitation of water vapour and/or aerosol within the circuit. These issues can cause circuit occlusions, interfere with ventilation settings and/or cause patient discomfort through nasal prongs splutter.

By controlling humidity levels such that the gas isn't saturated when it reaches the nebuliser the apparatus can increase the amount of drug reaching the patient by reducing precipitation of water vapour and/or aerosol within the circuit This mechanism has the additional benefit of resulting in less precipitation being blown towards the patient causing discomfort, for example when there are large droplets exiting the nasal prongs.

The control algorithm executed by the controller 17 sets how much flow should go through each limb, and the valve/flow restrictor 6 adjusts to achieve these values. Furthermore, the controller monitors temperature and humidity as detected by the temperature and humidity sensor (16) and adjusts the temperature of the heater and/or humidifier such that the air reaching the patient achieves the user inputted/default temperature and humidity. The reason for positioning this sensor after the nebuliser is that as the nebuliser adds moisture it also has a slight cooling effect—in practice this means that the air reaching the nebuliser will have to be heated to slightly above the target temperature.

If there is 100% flow through the humidifier 7 the flow into the nebulizer 2 will have close to 100% relative humidity. This is acceptable, and indeed desirable, while the nebulizer is passively allowing flow without medication. However, when medication is being added by the nebulizer 2 the nebulizer input humidity is preferably less than 100%, say 68%. The nebulizer 2 then brings the humidity level up to 100% by aerosolizing the liquid medication. Hence an optimum balance of medication aerosolization and humidity is achieved. Humidifiers may achieve close to 100% relative humidity at low gas flow rates but in practice the higher the gas flow rate the further the air is from saturated.

The components of the system have digital outputs and inputs and the controller implements the following control scheme:

Nebuliser Output (ml/min)/Target Humidity Level (ml/l) =Gas Flow Rate through Heat only Limb (l/min)

Target Gas Flow Rate (ml/min)/Gas Flow Rate through Heat only Limb (l/min)=Gas Flow Rate through Heated + Humified Limb (l/min)

The flow/pressure sensor 5 measures the gas flow entering the circuit. It then transmits this information to the controller 17. The gas flow entering the system is set typically on an external gas flow regulator, however, for greater control and convenience another flow restrictor/valve could be incorporated immediately after the sensor 5. The controller 17 then performs a calculation based on the information received from the sensor 5 as to how much gas should be directed through each limb. Target temperature and/or humidity are factored into this calculation and may be clinician set or pre-programmed.

In order to calculate the temperature and humidity levels required to achieve target temperature and humidity levels post aerosol inclusion the controller 17 authenticates that a nebulizer is connected and that it is actively aerosolizing. It also authenticates the nebuliser output rate to calculate the required flow split down each limb. This authentication may be achieved by:

Plume detection, such as by a vision system with a camera which monitors the extent of plume in the immediate vicinity of the nebulizer. Such monitoring may for example use image processing techniques to monitor the overall plume size in a two-dimensional plane.

Continuous or intermittent measurement of the volume of medication remaining in the nebulizer reservoir. By assessing the rate at which the reservoir liquid volume decreases the controller calculates the nebulizer output rate.

The controller being programmed to assume a set value (e.g. 0.4 ml/min) that is representative of the average and expected nebulizer output rate.

Receiving a signal from a nebulizer with a capability to provide activation and operating level data.

Based on the nebulizer output rate information received the controller then calculates how much of the initial gas flow to split down each limb. This flow splitting is achieved by controlling the flow restrictor/valve 6. The sensor 16 also transmits information to the controller enabling it to set the humidifier and heater to appropriate temperatures.

In a summary of the electronic components interaction; all of the sensors send information to the controller, the controller authenticates this information and based on calculations it performs it transmits commands to the valves/flow restrictors and the humidifier and the heater components of the system to adjust to specific settings. The nebuliser and controller exchange information—the nebuliser transmits information indicating when it is nebulising and in some embodiments output rate. The controller sends the drive signal to the nebuliser.

It is envisaged that the controller could modify this drive signal to increase or decrease the nebuliser output rate if this was a preferred way of achieving 100% humidity for example if the drug is not required to be delivered fast. The algorithm accommodates this potential variable.

Target gas flow rate, target humidity and target temperature can be user inputs or can be pre-programmed to default values. Humidity and temperature reaching the patient will be verified by the sensor (16) post nebuliser and pre-patient.

In the table below (Table 1) there is a fixed nebuliser output, however in other control schemes it could also be measured or controlled. There are two target humidity values indicative of current understanding of the area, 44 mg/l (0.044 ml/l) which is typically considered optimal humidity and 32 mg/l (0.032 ml/l) which is often considered essential humidity. Optimal humidity is at 37° C. and essential humidity is at 31° C.

To take the example of a target gas flow rate to the patient of 40 l/min at optimal humidity levels (44 mg/l) for a nebuliser with an output rate of 0.4 ml/min. In this case 9.09 l/min would be directed down the heated only limb while 30.91 l/min would be directed down the heated and humidified limb. However, these proportions do not stay constant with increasing output (target gas flow). For example, at an overall system output of 100 l/min at optimal humidity levels (44 mg/l) for a nebuliser with an output rate of 0.4 ml/min 9.09 l/min would still be directed down the heated only limb but now 90.91 l/min will be directed down the humidifier limb.

TABLE 1

Example of gas flow rate spit by limb for a specified nebuliser output rate for varying gas flow rates across two different target humidity levels.

| Target Humidity Level (ml/l) | Nebuliser Output (ml/min) | Target Gas Flow Rate (l/min) | Heat Only Limb Gas Flow Rate (l/min) | Heated + Humidified Limb Gas Flow Rate (l/min) |
|---|---|---|---|---|
| 0.032 | 0.4 | 10 | 10.00 | 0.00 |
| 0.044 | 0.4 | 10 | 9.09 | 0.91 |
| 0.032 | 0.4 | 20 | 12.50 | 7.50 |

TABLE 1-continued

Example of gas flow rate spit by limb for a specified nebuliser output rate
for varying gas flow rates across two different target humidity levels.

| Target Humidity Level (ml/l) | Nebuliser Output (ml/min) | Target Gas Flow Rate (l/min) | Heat Only Limb Gas Flow Rate (l/min) | Heated + Humidified Limb Gas Flow Rate (l/min) |
|---|---|---|---|---|
| 0.044 | 0.4 | 20 | 9.09 | 10.91 |
| 0.032 | 0.4 | 40 | 12.50 | 27.50 |
| 0.044 | 0.4 | 40 | 9.09 | 30.91 |
| 0.032 | 0.4 | 80 | 12.50 | 67.50 |
| 0.044 | 0.4 | 80 | 9.09 | 70.91 |
| 0.032 | 0.4 | 100 | 12.50 | 87.50 |
| 0.044 | 0.4 | 100 | 9.09 | 90.91 |

In an embodiment with integrated components the controller will authenticate from the flow/pressure sensor 5 how much flow is entering the system and the flow from the nebuliser 2 if aerosol is being produced and if so at what rate. It will then calculate what percentage humidity is required (for the selected gas flow rate) to reach the nebuliser such that when combined with nebuliser aerosol output the gas reaching the patient is optimal (44 mg/l @ 37° C.) or achieving the user specified levels and at the clinician-inputted (or automatic) temperature. This essentially determines what proportion of gas entering the system must pass through the heater 11 and what proportion must pass through the humidifier 7. Based on this information the flow will be restricted by the valve 6 to ensure this split. When the dose is delivered 100% of flow will pass through the humidifier 7.

The following are the approximate parameter values for one exemplary embodiment:
Optimal humidity: 44 mg/l @ 37° C. (0.044 ml/l assuming water vapour)
Gas flow rate entering system: 30l/min
Nebuliser output rate: 0.4 ml/min The nebuliser can bring ~10l/min up to optimal humidity levels. Therefore, for the entire 30l/min to reach optimal humidity levels 20l/min must pass through the heated and humidified limb 7 and 10l/min through the heater-only limb.

It will be appreciated that by having a "dry" branch and a humidifier branch there can be continuously an optimum split between the two for optimum gas flow to the patient.

Referring to FIG. 2 an alternative approach is illustrated, with only one supply to the nebuliser. A humidifier 50 has a housing 51 for air flow and it incorporates:
a heater 52,
an insulating layer 53, and
a water layer 54.

This arrangement allows humidity level to be controlled by controlling supply of water to be vaporised/evaporated. The porous heater plate controls temperature and the rate at which water is pumped up to it/made available to it controls humidity.

The humidifier has a controller, not shown, which dynamically varies water flow rate and heater operating parameters in order to control the level of humidification and temperature. This achieves, in a single flow to the nebuliser input, the level of control achieved by the two branches of the system 1.

It will be appreciated that the invention overcomes the existing problem of air passing through a standard humidified circuit being ~100% humidified, thus decreasing the aerosol carrying capacity of the air—increasing precipitation within the circuit, with resultant decrease in efficiency of therapeutic aerosol delivery. It can create an aerosol "window" in which the humidity of the air reaching the nebulizer is decreased to a level less than 100% so that when aerosol is added the air is 100% humidified. This should serve to decrease aerosol losses due to precipitation from insufficient gas carrying capacity. When humidification levels are stepped down heating of standard circuit heating wires would be increased.

The humidity level reaching the nebulizer is controlled by either limiting liquid availability (FIG. 2) or through the ratio of gas directed through a heated and humidified limb versus a humidified only limb (FIG. 1). The optimal level of humidity reaching the nebuliser is calculated based on gas flow rate, clinician inputs (desired temperature and desired humidity level), and potentially nebuliser output rate. Nebuliser output rate may be assumed to be constant, actively measured, or communicated by clinician or integrated tag.

A benefit is that humidity levels are maintained and that droplet size is decreased due to heating in a reduced humidity environment. Smaller droplets are more likely to reach the patient.

It is our understanding that heating tends to reduce the droplet size, thereby improving the delivery efficiency, particularly for low humidity. Also, by dynamically keeping the humidity at or just below 100% the level of precipitation is reduced.

The invention is not limited to the embodiments described but may be varied in construction and detail. For example, it is not essential that the nebulizer bring the relative humidity up to about 100%, it may be a different value which is desired for optimum therapy. The term "medication" covers any substance added to the nebulizer gas flow, including any liquid such as water, saline, or therapeutics.

The invention claimed is:

1. A method of controlling an aerosol delivery system having a nebulizer and a humidifier for a gas flow to the nebulizer, the method comprising:
controllably varying a humidity level of the gas flow to the nebulizer during an active nebulization phase using a two-branch inlet, a first branch including a flow restrictor and a heater and a second branch including the humidifier, and
wherein the varying of the humidity level is based on an output rate of the nebulizer.

2. The method of claim 1, wherein the output rate is used to control a percentage of flow through each branch of the two-branch inlet by adjusting an amount of flow through the flow restrictor.

3. The method of claim 1, wherein the output rate is used to control a percentage of flow through each branch of the two-branch inlet by adjusting an amount of flow through two flow restrictor valves.

4. The method of claim 3, wherein the output rate of the nebulizer is a set value.

5. The method of claim 4, wherein the output rate is authenticated to calculate percentage of flow through each branch.

6. The method of claim 1, wherein the output rate is actively measured.

7. The method of claim 6, wherein the output rate based on a volume of medication remaining in a reservoir of the nebulizer.

8. The method of claim 7, wherein the measurement is continuous.

9. The method of claim 1, wherein the humidity is controlled between 60 and 70%.

10. A method for optimizing an amount of medication delivered to a patient, comprising:
operating a system with two branches: a first branch including a heater and a second branch including a humidifier;
determining an amount of flow entering each branch of the system using a sensor;
controlling the amount of flow entering each branch using a flow restricting valve;
calculating a nebulizer input humidity level required within a gaseous mixture to reach a nebulizer such that when combined with a nebulizer aerosol output the gaseous mixture reaches a patient at a target humidity level, wherein
when the nebulizer is delivering medication, the nebulizer input humidity level is dynamically controlled by controlling a position of the flow restricting valve to vary flow to the first branch and the second branch, and
the determination of a required variation of the nebulizer input humidity level is based on a difference between a measured humidity level downstream of the nebulizer and the target humidity level.

11. The method of claim 10, wherein the measured humidity level is brought to 100% by the nebulizer.

12. The method of claim 10, wherein the nebulizer input humidity level is less than 85%.

13. The method of claim 12, wherein the nebulizer input humidity level is less than 70%.

14. The method of claim 10, wherein when the nebulizer is passively allowing flow without adding medication to the flow, the nebulizer input humidity level is greater than 95%.

15. The method of claim 10, further comprising measuring a volume of medicament within a reservoir of the nebulizer to determine a nebulizer output rate, the nebulizer output rate serving as an input to the control of an amount of flow entering each branch.

16. The method of claim 15, wherein the measurement of the medicament within the reservoir is intermittent.

17. A method of controlling an aerosol delivery system, comprising:
sensing a first humidity level of a gas flow at an exit of a nebulizer of a gas flow circuit and an output rate of the nebulizer; and
based on the sensing of the first humidity level of the gas flow at the exit of the nebulizer and the output rate of the nebulizer, adjusting a proportion of a gas flow entering a humidification branch of the gas flow circuit upstream of the nebulizer to actively vary a second humidity level of a gas flow to the nebulizer such that the first humidity level of the gas flow at the exit of the nebulizer is maintained at about 100% when (1) the nebulizer is actively delivering aerosol to the gas flow circuit, and (2) when the nebulizer is not delivering aerosol to the gas flow circuit;
wherein actively varying the second humidity level comprises continually sensing the first humidity level of the gas flow at the exit of the nebulizer and the output rate of the nebulizer and continually adjusting the proportion of the gas flow entering the humidification branch based on the sensing of the first humidity level of the gas flow at the exit of the nebulizer and the output rate of the nebulizer.

18. The method of claim 17, wherein the gas flow circuit comprises different branches including:
a heating branch including a heater; and
the humidification branch including a humidifier,
wherein the proportion of the gas flow entering the humidification branch is adjusted using a controllable, flow restricting valve.

19. The method of claim 17, wherein the second humidity level is reduced when the nebulizer is active.

20. The method of claim 19, wherein the second humidity level is less than 70% when the nebulizer is active.

* * * * *